(12) United States Patent
Pfleiderer et al.

(10) Patent No.: US 6,858,612 B1
(45) Date of Patent: Feb. 22, 2005

(54) USE OF TETRAHYDROPTERIDINE DERIVATIVES AS NO SYNTHASE INHIBITORS

(75) Inventors: Wolfgang Pfleiderer, Constance (DE); Harald Schmidt, Dettelbach (DE); Rainer Henning, Tokyo (JP)

(73) Assignee: Vasopharm Buitech GmbH, Wurzburg (DE)

( * ) Notice: Subject to any disclaimer, the term of this patent is extended or adjusted under 35 U.S.C. 154(b) by 0 days.

(21) Appl. No.: 09/357,212

(22) Filed: Jul. 20, 1999

Related U.S. Application Data

(63) Continuation of application No. 08/750,011, filed as application No. PCT/EP95/01785 on May 11, 1995, now abandoned.

(30) Foreign Application Priority Data

May 24, 1994 (DE) .......................................... 44 18 097

(51) Int. Cl.[7] ...................... A61K 31/495; A61K 31/50; A61P 9/00; A61P 25/28; A61P 7/00
(52) U.S. Cl. ...................... 514/249; 544/251; 544/258; 544/260
(58) Field of Search ......................... 514/249; 544/258, 544/260, 251

(56) References Cited

U.S. PATENT DOCUMENTS

| | | | |
|---|---|---|---|
| 4,665,182 A | 5/1987 | Nichol et al. ............... | 544/258 |
| 4,701,455 A | 10/1987 | Nichol et al. ............... | 514/249 |
| 4,937,342 A | 6/1990 | Kurono et al. .............. | 544/258 |
| 5,196,533 A | 3/1993 | Ayling et al. ............... | 544/118 |
| 5,502,050 A | 3/1996 | Gross ......................... | 514/241 |
| 5,753,656 A | 5/1998 | Sakai .......................... | 514/249 |

FOREIGN PATENT DOCUMENTS

| | | | |
|---|---|---|---|
| JP | 6-56669 | * | 3/1994 |
| WO | 94 14780 | | 7/1994 |
| WO | 95 32203 | | 11/1995 |

OTHER PUBLICATIONS

Macdonald, James E., Nitric Oxide Synthase Inhibitors, Annual Reports In Medicinal Chemistry, vol. 33, pp. 221–229, 1996.*
CAPLUS printout for Kojima, S., Neopterin As An Endogenous Antioxidant, Pteridines, vol. 6, No. 4, pp. 181–184, 1995.*
CAPLUS printout for Miwa et al., 6R–L–Erythro–5,6,7, 8–Tetrahydrobiopterin and Dopamine Release, Pteridines, vol. 6, No. 4, pp. 173–180, 1995.*

CAPLUS printout for JP 6–56669, 1994.*
Hevel et al., Macrophage Nitric Oxide Synthase: Relationship between Enzyme–Bound Tetrahydrobiopterin and Synthase Activity, vol. 31, No. 31, pp. 7160–7165, 1992.*
Natanson, Charles, et al., "Selected Treatment for Septic Shock Based on Proposed Mechanisms of Pathogenesis", Annals of Internal Medicine, vol. 120 (No. 9), 1994, pp. 771–783.
Werner–Falmayer et al., J. Exp. Med., vol. 172, Dec. 1990, pp. 1599–1607.
Schoedon, et al., Biochemical & Biophysical Research Communication, vol. 199, No. 2, Mar. 15, 1994, pp. 504–510.
Sakai, Naoki et al., $BH_4$ and NO Synthesis, Vo. 48(1), pp. 6–10, 1993.
Gunther, Konrad et al., Chem. Ber., 103, 1970, pp. 722–734.
Jorens, Philippe et al., Br. J., Pharmacol, 1992, 107, pp. 1088–1091.
Traub, Hermann, "Synthese Und Eigenschaften Von Tetrahydrobiopterin–Analogen Potentielle Cofaktoren Für Biologishe Hydroxylierungen", Dissertation for the University of Konstanz, May 1987.
Ege–Serdenkci et al., Chemical Abstracts, vol. 100, 1983, Entry 33933.
Amarego et al., Chemical Abstracts, vol. 100, 1983, Entry 50980.
Amarego et al., Chemical Abstracts, vol. 98, 1983, Entry 53504.

* cited by examiner

*Primary Examiner*—Brenda Coleman
(74) *Attorney, Agent, or Firm*—Finnegan, Henderson, Farabow, Garrett & Dunner, LLP

(57) ABSTRACT

The present invention relates to the use of pteridine derivatives of the formula I

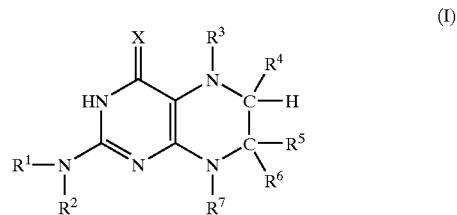

(I)

in which X is O or NH and $R^4$, for example, is hydrogen, phenyl or the radical $R^{4a}$—$CH_2$— and $R^{4a}$, for example, is hydrogen, $(C_1-C_4)$-alkylmercapto, the radical —$NR^{11}R^{12}$ or the radical —$OR^{13}$, and in which $R^1, R^2, R^3, R^5, R^6, R^7, R^{11}, R^{12}$ and $R^{13}$ have the meanings given in claim 1, which are nitric oxide synthase inhibitors, for the treatment of diseases which are caused by an increased nitric oxide level.

23 Claims, No Drawings

USE OF TETRAHYDROPTERIDINE DERIVATIVES AS NO SYNTHASE INHIBITORS

This is a continuation of application Ser. No. 08/750,011, filed Nov. 21, 1996, abn. which is a U.S. National Phase Application of PCT/EP95/01785, filed May 11, 1995, all of which are incorporated herein by reference.

The present invention relates to pteridine derivatives of the formula I

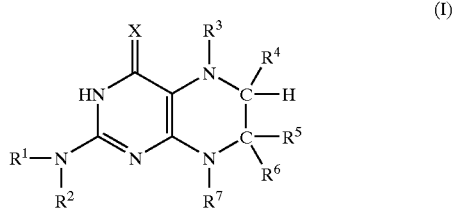

which on account of their ability to modulate endogenous nitric oxide production are useful pharmaceuticals for the prevention and control of states which are characterized by a disturbed nitric oxide level.

Nitric oxide (NO) plays an important part in all sorts of physiological processes (see, for example, R. Henning, Nachr. Chem. Tech. Lab. 41 (1993), 413; H. H. H. W. Schmidt et al., Biochim. Biophys. Acta 1178 (1993), 153).

It has, for example, a relaxing effect on the smooth vascular musculature and in this way is substantially involved in the regulation of blood pressure. It controls blood clotting via inhibition of platelet aggregation, and it is involved, for example, as a neurotransmitter in the brain in the building up of long-term memory. NO also functions as a messenger substance in the NANC nerves of the peripheral nervous system. The cytotoxic action of NO is utilized by macrophages for defense against infection.

Endogenous NO is formed from arginine with the aid of at least three different NO synthase isoenzymes (see, for example, J. F. Kerwin, Jr., M. Heller, Med. Res. Rev. 14 (1994), 23). They differ with respect to their localization in the body, their regulability by $Ca^{2+}$/calmodulin and their inducibility by endotoxins and cytokines. The constitutive, calcium-dependent NO synthases are found, for example, in endothelium (Type III) and in the brain (Type I) and are involved there in the regulation of blood pressure and coagulation and in the conduction process. The cytokine-inducible, calcium-independent isoform (Type II) occurs in macrophages, smooth muscle cells and hepatocytes. It is able, over the long term, to produce relatively large amounts of NO and is held responsible for inflammatory processes and the cytotoxic activity of the macrophages.

A disturbed NO balance results in serious disorders and damage. Thus excessive formation of NO in septic or hemorrhagic shock leads to massive pathological blood pressure decreases. Excess NO production is involved in the formation of type I diabetes and atherosclerosis and also appears to be responsible for glutamate-induced neurotoxicity after cerebral ischemia. High NO concentrations can moreover lead to DNA damage as a result of deamination of cytosine. Examples of disorders which are caused indirectly or directly by a lack of endogenous NO are arterial high blood pressure, hemostasis disorders, coronary heart disease and erectile dysfunction.

The attempt to use modulation of NO production for the treatment of these syndromes has until now only been realized with the aid of arginine analogs (GB-A-2240041; WO-A-93/13055). Further potential NO synthase inhibitors discussed in the literature are N-iminoethylornithine (McCall et al., Br.J.Pharmacol. 102 (1991), 234), aminoguanidine (T. P. Misko et al., Eur.J.Pharmacol. 233 (1993), 119; EP-A-547588) and 7-nitroindazole (P. K. Moore et al., Br.J.Pharmacol. 108 (1993), 296).

Various pteridine derivatives occur in nature, and uses of pteridine derivatives as pharmaceutical active compounds have also been described. Thus EP-B-108 890 relates to the use of pteridine derivatives for the treatment of diseases which can be attributed to a catecholamine deficiency, such as, for example, Parkinson's disease, and the use of pteridines for the treatment of phenylketonuria (see also E. C. Bigham et al., Chemistry and Biology of Pteridines (1986) S.111, Walter de Gruyter & Co., Berlin, N.Y.); these also include certain compounds of the formula I in which X is oxygen and $R^1$, $R^2$, $R^3$ and $R^7$ are simultaneously hydrogen. The action of the naturally occurring 5,6,7,8-tetrahydrobiopterin and of analogs of this substance on NO production was studied, for example, by Kwon et al. (J.Biol.Chem. 264 (1989), 20496) or Giovanelli et al. (Proc.Natl.Acad.Sci. USA 88 (1991), 7091). Accordingly, tetrahydrobiopterin stimulates NO production and is a cofactor of NO synthases. Stimulation of NO production was also found for 7,8-dihydrobiopterin. According to Overfeld et al. (Br.J.Pharmacol. 107 (1992), 1008), 5,6,7,8-tetrahydrobiopterin, however, can also have an inhibitory effect on NO production. The effect is concentration-dependent.

Hevel and Marletta (Biochemistry 31 (1992), 7160) reports on an increase in NO synthase activity due to 6-methyl-5,6,7,8-tetrahydropterin. This was only observed at relatively high concentrations by Giovanelli et al. (loc. cit.). Various other petals derivatives showed no significant effects in these studies.

Surprisingly, it has now been found that pteridine derivatives of the formula I, in particular, have an inhibiting modulatory effect on endogenous NO production and are thus suitable as pharmaceuticals in diseases which are characterized by an excessive NO level.

The present invention relates to the use of pteridine derivatives of the formula I

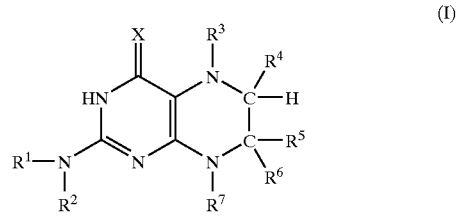

in which

X is O or NH;

$R^1$ is hydrogen, methyl, $(C_1-C_5)$-alkanoyl, nicotinoyl or (1-methyl-3-pyridinio)carbonyl;

$R^2$ is hydrogen or methyl;

$R^3$ is hydrogen, methyl, ethyl, benzyl, $(C_1-C_5)$-alkanoyl, unsubstituted benzoyl, substituted benzoyl, pyridoyl, thienylcarbonyl, one of the radicals

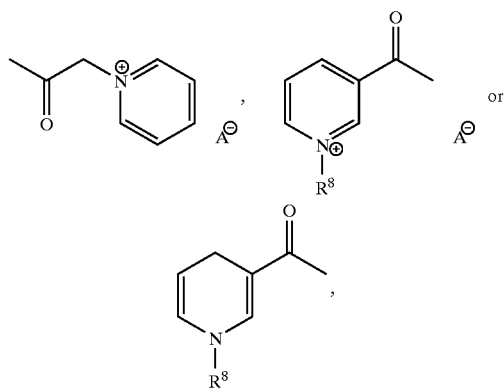

the radical $R^9R^{9a}N$—CO—, the radical $R^9R^{9a}N$—CS—, phenoxycarbonyl or benzyloxycarbonyl;

$R^4$ is hydrogen, $(C_2-C_5)$-alkyl, unsubstituted phenyl, substituted phenyl or the radical $R^{4a}$—$CH_2$—;

$R^{4a}$ is hydrogen, $(C_1-C_4)$-alkylmercapto, the radial —$S(O)_mR^{10}$, where m is the numbers 1 or 2, the radical $NR^{11}R^{12}$ or the radical —$OR^{13}$, or $R^3$ and $R^{4a}$ together are the group —CO—O—, its carbonyl carbon atom being bonded to the 5-position of the pteridine molecule;

$R^5$ is hydrogen, methyl or phenyl;

$R^6$ is hydrogen or methyl;

$R^7$ is hydrogen or methyl;

$R^8$ is $(C_1-C_{10})$-alkyl or benzyl;

$R^9$ is hydrogen, $(C_1-C_6)$-alkyl, cyclohexyl, phenyl or benzoyl;

$R^{9a}$ is hydrogen, methyl or ethyl;

$R^{10}$ is methyl;

$R^{11}$ and $R^{12}$ independently of one another are hydrogen or methyl;

$R^{13}$ is hydrogen, $(C_1-C_{10})$-alkyl, 2-methoxyethyl, phenyl, 3-phenylpropyl, 3-cyclohexylpropyl, $(C_1-C_5)$-alkanoyl, hydroxyacetyl, 2-amino-$(C_2-C_6)$-alkanoyl which is unsubstituted or substituted in the alkyl moiety by a phenyl radical, or $((C_1-C_2)$-alkoxy)carbonyl;

$A^\ominus$ is a pharmacologically tolerable anion;

and their tautomeric forms and their pharmacologically tolerable salts for the prevention and treatment of diseases which are caused by an increased nitric oxide level.

Alkyl groups can be straight-chain or branched. This also applies if they occur in other groups, for example in alkoxy, alkylmercapto, alkoxycarbonyl or alkanoyl groups. Examples of alkyl groups which can occur in the compounds of the formula I to be used according to the invention as such, i.e. as $(C_1-C_4)$-, $(C_2-C_5)$-, $(C_1-C_6)$- or $(C_1-C_{10})$-alkyl, or in other groups, are methyl, ethyl, n-propyl, i-propyl, n-butyl, i-butyl, sec-butyl, tert-butyl, n-pentyl, 3-methylbutyl, 2,2-dimethylpropyl, n-hexyl, n-heptyl, n-octyl, n-nonyl or n-decyl. Examples especially of $(C_1-C_5)$-alkanoyl are formyl, acetyl, propionyl, n-butyryl, i-butyryl, n-valeroyl, 3-methyl-n-butyryl or 2,2-dimethylpropionyl. Examples of $(C_1-C_2)$-alkoxy are methoxy and ethoxy. Examples of 2-amino-$(C_2-C_6)$-alkanoyl which is unsubstituted or substituted in the alkyl moiety by a phenyl radical are the corresponding radicals of the amino acids glycine, alanine, valine, leucine, isoleucine, norvaline, norleucine, phenylglycine or phenylalanine.

Substituted phenyl groups and benzoyl groups can be mono- or polysubstituted, preferably they are mono- to trisubstituted. The substituents can be located in any desired positions, an individual substituent, for example, in the ortho-, meta- or para-position. In the case of multiple substitution, the substituents can be identical or different. Substituents which can be present, for example, are $(C_1-C_4)$-alkyl, $(C_1-C_4)$-alkoxy, amino, $(C_1-C_4)$-alkylamino, di-$((C_1-C_4)$-alkyl)amino, $(C_1-C_5)$-alkanoylamino, nitro or halogen, where only up to two nitro groups can be present. Halogen is, for example, fluorine, chlorine, bromine or iodine.

Pyridoyl can be 2-, 3- or 4-pyridoyl, 3-pyridoyl (=nicotinoyl) being preferred. Thienylcarbonyl can be 2- or 3-thienylcarbonyl.

Examples of acids of the formula HA whose anion can be present in the compounds of the formula I to be used according to the invention are hydrochloric acid, hydrobromic acid, hydriodic acid, sulfuric acid, phosphoric acid, nitric acid, methanesulfonic acid, toluenesulfonic acid, acetic acid, propionic acid, benzoic acid, lactic acid, tartaric acid, citric acid, maleic acid and fumaric acid. $A^\ominus$, however, can also be an anion of another inorganic or organic acid which is suitable from pharmacological and pharmaceutical points of view and can, if the compound of the formula I is present in the form of an acid addition salt, correspond to the anion introduced by this salt formation or differ therefrom.

The compounds of the formula I can be present in various tautomeric forms and in various stereoisomeric forms. The present invention comprises not only the use of all tautomeric forms, but also that of all stereoisomeric forms, i.e., for example, that of pure enantiomers, of enantiomer mixtures and racemates, of pure diastereomers and diastereomer mixtures or of cis/trans isomers.

X is preferably oxygen.

Preferably, $R^1$ and $R^2$ are simultaneously hydrogen or simultaneously methyl, or $R^2$ is hydrogen and $R^1$ is simultaneously $(C_1-C_5)$-alkanoyl, in particular acetyl, i-butyryl or pivaloyl, or nicotinoyl or (1-methyl-3-pyridinio)carbonyl. Particularly preferably, $R^1$ and $R^2$ are simultaneously hydrogen or $R^2$ is hydrogen and $R^1$ is simultaneously i-butyryl.

$R^3$ is preferably hydrogen or an acyl radical or a (thio) carbamoyl radical. Acyl radicals are in this case preferably understood as meaning $(C_1-C_5)$-alkanoyl, in particular formyl, acetyl and pivaloyl, unsubstituted or mono-, di- or trisubstituted benzoyl, thienylcarbonyl, as well as nicotinoyl and the radicals

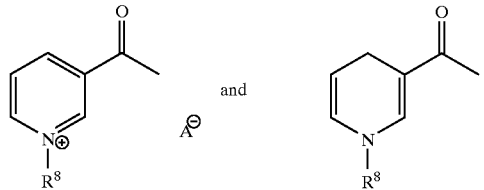

where $R^8$ is preferably methyl, n-octyl or benzyl and preferred substituents in substituted benzoyl groups are halogen and methoxy. In the carbamoyl radicals $R^9R^{9a}N$—CO—, $R^9$ is preferably hydrogen, $(C_1-C_4)$-alkyl, in particular tert-butyl, as well as cyclohexyl and phenyl and $R^{9a}$ is simultaneously hydrogen, or $R^9$ and $R^{9a}$ are simultaneously methyl. In the thiocarbamoyl radicals $R^9R^{9a}N$—CS—, $R^9$ is preferably hydrogen, $(C_1-C_4)$-alkyl, in particular methyl or ethyl, as well as phenyl and benzoyl and $R^{9a}$ is simultaneously hydrogen. Particularly preferably, $R^3$ is hydrogen, the N-phenylthiocarbamoyl radical, the unsubstituted benzoyl radical, the niclotinoyl radical or a 3-pyridinocarbonyl radical derived from the latter by alkylation or benzylation on the nicotinoyl nitrogen or a 1,4-dihydro-3-pyridylcarbonyl radical alkylated or benzylated in the 1-position of the pyridine ring.

$R^4$ is preferably hydrogen, phenyl, phenyl substituted by an acetylamino group, in particular by a para-acetylamino group, or the radical $R^{4a}$—$CH_2$—.

$R^{4a}$ is preferably hydrogen or the radical —$OR^{13}$. If $R^4$ is hydrogen or $R^{4a}$ is hydrogen, it is particularly preferred if $R^3$ is simultaneously an acyl radical or a (thio)carbamoyl radical.

$R^5$ is preferably hydrogen.
$R^7$ is preferably hydrogen.
$R^{9a}$ is preferably hydrogen.
$R^{13}$ is preferably hydrogen, $(C_1-C_{10})$-alkyl or an acyl radical, in particular $(C_1-C_5)$-alkanoyl or 2-amino-$(C_2-C_6)$-alkanoyl which is unsubstituted or substituted in the alkyl moiety by a phenyl radical. Particularly preferably, $R^{13}$ is $C_1-C_{10}$-alkyl or $(C_1-C_5)$-alkanoyl, especially acetyl. If $R^{13}$ is $(C_1-C_{10})$-alkyl, n-alkyl radicals as well as i-propyl, i-butyl and tert-butyl are preferred.

Use of compounds of the formula I is preferred in which one or more substituents have preferred meanings. Use of pteridine derivatives of the formula Ia is furthermore preferred

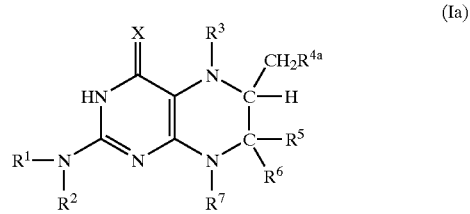

(Ia)

in which
X is O or NH;
$R^1$ is hydrogen, methyl, $(C_1-C_5)$-alkanoyl, nicotinoyl or (1-methyl-3-pyridinio)carbonyl;
$R^2$ is hydrogen or methyl;
$R^3$ is hydrogen, methyl, ethyl, benzyl, $(C_1-C_5)$-alkanoyl, benzoyl, nicotinoyl, one of the radicals

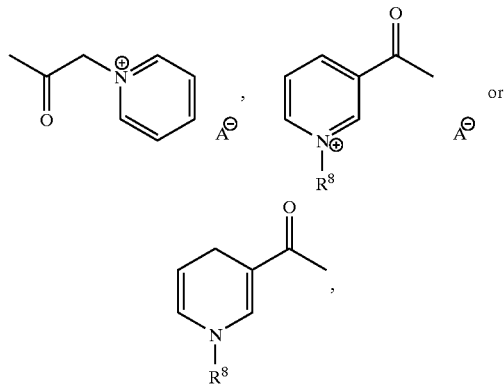

the radical $R^9NH$—CO—, the radical $R^9NH$—CS— or benzyloxycarbonyl;
$R^{4a}$ is hydrogen, $(C_1-C_4)$-alkylmercapto, the radical —$S(O)_mR^{10}$, where m is the numbers 1 or 2, the radical —$NR^{11}R^{12}$ or the radical —$OR^{13}$, or
$R^3$ and $R^{4a}$ together are the group —CO—O—, its carbonyl carbon atom being bonded to the 5-position of the pteridine molecule;

$R^5$ and $R^6$ independently of one another are hydrogen or methyl;
$R^7$ is hydrogen or methyl;
$R^8$ is $(C_1-C_{10})$-alkyl or benzyl;
$R^9$ is hydrogen, $(C_1-C_6)$-alkyl, cyclohexyl, phenyl or benzoyl;
$R^{10}$ is methyl;
$R^{11}$ and $R^{12}$ independently of one another are hydrogen or methyl;
$R^{13}$ is hydrogen, $(C_1-C_{10})$-alkyl, 2-methoxyethyl, phenyl, 3-phenylpropyl, 3-cyclohexylpropyl, $(C_1-C_5)$-alkanoyl, hydroxyacetyl, 2-amino-$(C_2-C_6)$-alkanoyl which is unsubstituted or substituted in the alkyl moiety by a phenyl radical, or $((C_1-C_2)$-alkoxy)carbonyl;
$A^\ominus$ is a pharmacologically tolerable anion;
and their tautomeric forms and also their pharmacologically tolerable salts for the prevention and treatment of diseases which are caused by an increased nitric oxide level.

Particularly preferred compounds of the formula I to be used according to the invention are those in which $R^1$, $R^2$, $R^3$, $R^5$, $R^6$ and $R^7$ simultaneously are hydrogen and $R^4$ is the radical $R^{4a}$—$CH_2$— and, in this, $R^{4a}$ is an amino group, a methylamino group, a dimethylamino group, a $(C_1-C_{10})$-alkyloxy group or an acetoxy group. Compounds particularly preferably to be used are furthermore those in which $R^2$, $R^4$, $R^5$, $R^6$ and $R^7$ are simultaneously hydrogen, $R^1$ is hydrogen or isobutyryl and $R^3$ is an acyl radical or a (thio)carbamoyl radical. A further group of compounds of the formula I particularly preferably to be used are those in which $R^2$, $R^6$ and $R^7$ are simultaneously hydrogen, $R^1$ is hydrogen or isobutyryl, $R^3$ is an acyl radical, $R^4$ is phenyl or phenyl substituted by an acetylamino group, in particular a para-acetylamino group, and $R^5$ is hydrogen or phenyl.

The compounds of the formula I are known and can be prepared according to or analogously to known processes. Known synthesis methods for pteridine derivatives of the formula I are, for example, the method of Gabriel-Isay or the Taylor method (see, for example, D. J. Brown, Fused Pyrimidines III, Pteridines (E. C. Taylor and A. Weissberger (Ed.), Wiley & Sons, New York)). In detail, the preparation of compounds of the formula I is described, for example, in EP-A-108 890, in the thesis of Hermann Michael Traub (Dissertation der Universität Konstanz, Deutschland (1987)), or in J. Med. Chem. 30 (1987), 40.

The compounds of the formula I to be used according to the invention can form salts with inorganic or organic acids. Suitable acids for the formation of pharmacologically acceptable acid addition salts are, for example: hydrochloric acid, hydrobromic acid, naphthalenedisulfonic acids, in particular 1,5-naphthalenedisulfonic acid, or phosphoric, nitric, sulfuric, oxalic, lactic, tartaric, acetic, salicylic, benzoic, formic, propionic, pivalic, diethylacetic, malonic, succinic, pimelic, fumaric, maleic, malic, sulfamic, phenylpropionic, gluconic, ascorbic, isonicotinic, methanesulfonic, p-toluenesulfonic, citric or adipic acid. The compounds of the formula I can add one or more, e.g. two or three, in particular two, acid equivalents. The acid addition salts can be prepared in the customary manner by combination of the components, expediently in a suitable solzent or diluent. Acid addition salts can be converted into one another by anion exchange. $A^\ominus$ can likewise be an anion of one of the acids mentioned. Compounds of the formula I which can contain acidic groups can form salts with inorganic or organic bases. Examples of such salts are, for example, alkali metal salts, in particular sodium and potassium salts, or ammonium salts, in particular those with organic radicals on the ammonium nitrogen.

The inhibition of NO release by the compounds of the formula I can be determined by an activity assay based on the studies of Bredt and Snyder and also Schmidt et al. (see D. S. Bredt and S. S. Snyder, Isolation of nitric oxide synthase, a calmodulin-requiring enzyme, Proc. Natl. Acad. Sci. USA 87 (1990), 682; H. H. H. W. Schmidt et al., Purification of a soluble isoform of guanylyl cyclase-activating factor synthase, Proc. Natl. Acad. Sci. USA 88 (1991), 365). In this assay for purified NO synthase (NOS) the coproduct L-citrulline obtained during NO formation is determined quantitatively. This is carried out by the use of $^3$H-radiolabelled L-arginine as a substrate of the enzyme reaction, which is reacted to give $^3$H-L-citrulline and NO. After the enzyme incubation is complete, resulting L-citrulline is removed from unused L-arginine by means of ion-exchange chromatography of the reaction mixture; the $^3$H-activity determined by liquid scintillation measurement then corresponds to the amount of L-citrulline. Details of the procedure are given further below.

Diseases which arise due to an increased NO level and which can thus be treated according to the invention with the compounds of the formula I or which can be prevented using these, are, in particular, pathological blood pressure decreases, such as occur in septic or hemorrhagic shock, in tumor or cancer therapy with cytokines or in cirrhosis of the liver. In addition, inflammatory disorders, such as rheumatoid arthritis and in particular ulcerative colitis, as well as insulin-dependent diabetes mellitus and transplant rejection reactions.

However, the following disorders are also connected with increased production of nitric oxide and can be treated or prevented according to the invention. In the cardiovascular field, these are arteriosclerosis, post-ischemic tissue damage and infarct damage, reperfusion damage, myocarditis based on a Coxsackie virus infection and cardiomyopathy; in the nervous system/central nervous system field they are neuritides of varying etiogeneses (forms of neuritis), encephalomyelitides, viral neurodegenerative disorders, Alzheimer's disease, hyperalgesia, epilepsy and migraine; in the kidney field they are acute kidney failure and nephritides of varying etiogeneses, especially glomerulonephritis.

Additionally, treatments in the stomach and the uterus/placenta field and also affecting sperm motility are also fields of use for the compounds of the formula I.

The compounds of the formula I and their pharmacologically acceptable salts can be employed in research and in diagnostic processes as auxiliaries in biochemical and pharmacological studies, and they can be administered to animals, preferably to mammals, and in particular to humans as therapeutics per se, as mixtures with one another or in the form of pharmaceutical preparations which allow enteral or parenteral use and which as active constituent contain an effective dose of at least one compound of the formula I or a salt thereof, in addition to customary pharmaceutically innocuous excipients and additives.

The therapeutics can be administered orally, e.g. in the form of pills, tablets, lacquered tablets, coated tablets, hard and soft gelatin capsules, solutions, syprups, emulsions or suspensions or aerosol mixtures. Administration, however, can also be carried out rectally, e.g. in the form of suppositories, or parenterally, e.g. in the form of injection solutions or infusion solutions, or percutaneously, e.g. in the form of ointments or tinctures.

In addition to the active compounds and excipients, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and further solvents or solubilizers or agents for achieving a depot effect, as well as salts for changing the osmotic pressure, coating agents or anti-oxidants. They can also contain two or more compounds of the formula I or their pharmacologically acceptable salts and also other therapeutically active substances.

Other therapeutically active substances of this type are, for example: β-receptor blockers, such as, for example, propranolol, pindolol, metoprolol; vasodilators, such as, for example, carbocromene; tranquillizers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosin, clonidine, Rauwolfia alkaloids; agents which lower the fatty acid level in the blood, such as, for example, bezafibrate, fenofibrate; agents for thrombosis prophylaxis, such as, for example, phenprocoumon; anti-inflammatory substances, such as, for example, cortico-steroids, salicylates or propionic acid derivatives, such as, for example, ibuprofen; antibiotics, such as, for example, penicillins or cephalosporins; NO donors, such as, for example, organic nitrates or sydnone imines or furoxanes.

The dose can vary within wide limits and is to be suited to the individual conditions in each individual case. In general, a daily dose of approximately 0.5 to 100 mg; preferably 1 to 20 mg, per human individual is appropriate in the case of oral administration. In the case of other administration forms too, the daily dose is in similar ranges of amounts, i.e. in general likewise at 0.5 to 100 mg/person. The daily dose can be divided into several, e.g. 2 to 4, part administrations.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

Until now, no pharmacological effects or medicinal uses were known for various pteridine derivatives of the formula I. For such compounds, the present invention gives the first medicinal indication. The present invention also relates to pteridine derivatives of the formula I

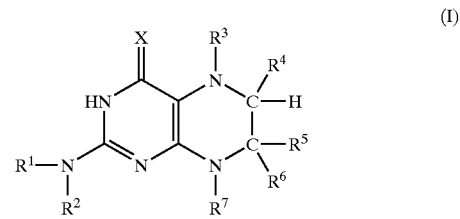

in which

X is O or NH;

$R^1$ is hydrogen, methyl, ($C_1$–$C_5$)-alkanoyl, nicotinoyl or (1-methyl-3-pyridinio)carbonyl;

$R^2$ is hydrogen or methyl;

$R^3$ is hydrogen, methyl, ethyl, benzyl, ($C_1$–$C_5$)-alkanoyl, unsubstituted benzoyl, substituted benzoyl, pyridoyl, thienylcarbonyl, one of the radicals

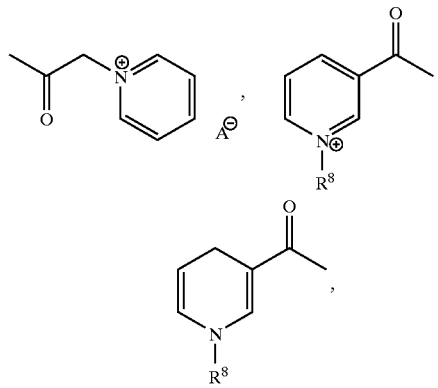

the radical $R^9R^{9a}$N—CO—, the radical $R^9R^{9a}$N—CS—, phenoxycarbonyl or benzyloxycarbonyl;

$R^4$ is hydrogen, ($C_2$–$C_5$)-alkyl, unsubstituted phenyl, substituted phenyl or the radical $R^{4a}$—$CH_2$—;

$R^{4a}$ is hydrogen ($C_1$–$C_4$)-alkylmercapto, the radical —S(O)$_m$R$^{10}$, where m is the numbers 1 or 2, the radical —NR$^{11}$R$^{12}$ or the radical —OR$^{13}$ or $R^3$ and $R^{4a}$ together are the group —CO—O—, its carbonyl carbon atom being bonded to the 5-position of the pteridine molecule;

$R^5$ is hydrogen, methyl or phenyl;

$R^6$ is hydrogen or methyl;

$R^7$ is hydrogen or methyl;

$R^8$ is ($C_1$–$C_{10}$)-alkyl or benzyl;

$R^9$ is hydrogen, ($C_1$–$C_6$)-alkyl, cyclohexyl, phenyl or benzoyl;

$R^{9a}$ is hydrogen, methyl or ethyl;

$R^{10}$ is methyl;

$R^{11}$ and $R^{12}$ independently of one another are hydrogen or methyl;

$R^{13}$ is hydrogen, ($C_1$–$C_{10}$)-alkyl, 2-methoxyethyl, phenyl, 3-phenylpropyl, 3-cyclohexylpropyl, ($C_1$–$C_5$)-alkanoyl, hydroxyacetyl, 2-amino-($C_2$–$C_6$)-alkanoyl which is unsubstituted or substituted in the alkyl moiety by a phenyl radical, or (($C_1$–$C_2$)-alkoxy)carbonyl;

$A^\ominus$ is a pharmacologically tolerable anion;

and their tautomeric forms and also their pharmacologically tolerable salts where, however, if X is oxygen and at the same time $R^4$ is the radical $R^{4a}$—$CH_2$—, at least one of the substituents $R^1$, $R^2$, $R^3$ and $R^7$ has a meaning other than hydrogen, as pharmacological active compounds.

The following examples give compounds of the formula I which can be employed according to the invention. In the column "salts" is indicated how many moles of acid and how many moles of water of crystallization, if appropriate, were present per mole of active compound in the pteridine derivatives of the formula I. In the examples, the following abbreviations are used:

Me=methyl
Et=ethyl
iPr=isopropyl
iBu=isobutyl
tBu=tert-butyl
Ph=phenyl
Py=3-pyridyl

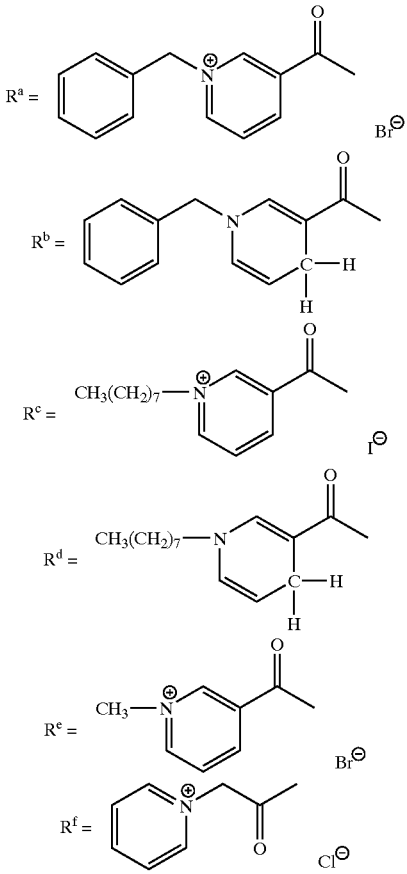

EXAMPLE 1

X=O
$R^1$=H
$R^2$=H
$R^5$=Me
$R^6$=H
$R^7$=H
$R^3$=H
$R^4$=Me

EXAMPLE 2

X=O
$R^1$=H
$R^2$=H
$R^5$=H
$R^6$=H
$R^7$=Me
$R^3$=H
$R^4$=Me

EXAMPLE 3

X=O
$R^1$=H
$R^2$=H $R^5$=H
$R^6$=H
$R^7$=Me
$R^3$=CHO
$R^4$=Me

EXAMPLE 4

X=O
$R^1$=H
$R^2$=H
$R^5$=Me
$R^6$=H
$R^7$=Me
$R^3$=CHO
$R^4$=Me

EXAMPLE 5

X=O
$R^1$=H
$R^2$=H
$R^5$=Me
$R^6$=H
$R^7$=H
$R^3$=CONH$_2$
$R^4$=Me
Salt: 0.5H$_2$O
m.p. 257° C.

EXAMPLE 6

X=O
$R^1$=H
$R^2$=H
$R^5$=Me
$R^6$=H
$R^7$=H
$R^3$=CSNHMe
$R^4$=Me
Salt: 1.5H$_2$O
m.p. 195° C.

EXAMPLE 7

X=O
$R^1$=H
$R^2$=H
$R^5$=Me
$R^6$=H
$R^7$=H
$R^3$=CSNHPh
$R^4$=Me
Salt: 2H$_2$O
m.p. 239° C.

EXAMPLE 8

X=O
$R^1$=H
$R^2$=H
$R^5$=Me
$R^6$=H
$R^7$=H
$R^3$=CSNHEt
$R^4$=Me
Salt: 2H$_2$O
m.p. 202° C.

EXAMPLE 9

X=O
$R^1$=H
$R^2$=H
$R^5$=Me
$R^6$=H
$R^7$=H
$R^3$=CSNHCOPh
$R^4$=Me
Salt: 0.5 H$_2$O
m.p. 229° C.

EXAMPLE 10

X=O
$R^1$=H
$R^2$=H
$R^5$=Me
$R^6$=H
$R^7$=H
$R^3$=CONHPh
$R^4$=Me
Salt: 1H$_2$O
m.p. 197° C. (dec.)

EXAMPLE 11

X=O
$R^1$=H
$R^2$=H
$R^5$=Me
$R^6$=H
$R^7$=H
$R^3$=CONHtBu
$R^4$=Me
Salt: 1H$_2$O
m.p. 260° C. (dec.)

EXAMPLE 12

X=O
$R^1$=H
$R^2$=H
$R^5$=Me
$R^6$=H
$R^7$=H
$R^3$=CONH-cyclohexyl
$R^4$=Me
Salt: 1H$_2$O
m.p. 242° C.

EXAMPLE 13

X=O
$R^1$=H

R² = H
R⁵ = Me
R⁶ = H
R⁷ = H
R³ = COPh
R⁴ = Me
m.p. >320° C.

EXAMPLE 14

X = O
R¹ = H
R² = H
R⁵ = Me
R⁶ = H
R⁷ = H
R³ = COPy
R⁴ = Me
m.p. 295° C.

EXAMPLE 15

X = O
R¹ = H
R² = H
R⁵ = Me
R⁶ = H
R⁷ = H
R³ = Rᵃ
R⁴ = Me
Salt: 0.5H₂O
m.p. 275° C.

EXAMPLE 16

X = O
R¹ = H
R² = H
R⁵ = Me
R⁶ = H
R⁷ = H
R³ = Rᵇ
R⁴ = Me
m.p. 255° C.

EXAMPLE 17

X = O
R¹ = H
R² = H
R⁵ = H
R⁶ = H
R⁷ = H
R³ = Rᵇ
R⁴ = Me
Salt: 1H₂O
m.p. 232° C.

EXAMPLE 18

X = O
R¹ = H
R² = H
R⁵ = Me
R⁶ = H
R⁷ = H
R³ = Rᶜ
R⁴ = Me
Salt: 0.5H₂O
m.p. 180° C.

EXAMPLE 19

X = O
R¹ = H
R² = H
R⁵ = H
R⁶ = H
R⁷ = H
R³ = COPy
R⁴ = Me
Salt: 1H₂O
m.p. 265–270° C.

EXAMPLE 20

X = O
R¹ = H
R² = H
R⁵ = H
R⁶ = H
R⁷ = H
R³ = Rᶜ
R⁴ = Me
m.p. 206–208° C.

EXAMPLE 21

X = O
R¹ = H
R² = H
R⁵ = Me
R⁶ = H
R⁷ = H
R³ = Rᵈ
R⁴ = Me
m.p. <200° C. (dec.)

EXAMPLE 22

X = O
R¹ = COiPr
R² = H
R⁵ = Me
R⁶ = H
R⁷ = H
R³ = COPy
R⁴ = Me
m.p. >300° C.

EXAMPLE 23

X = O
R¹ = COPy $R^2$=H
$R^5$=Me
$R^6$=H
$R^7$=H
$R^3$=COPy
$R^4$=Me
m.p. 325° C.

EXAMPLE 24

X=O
$R^1$=Me
$R^2$=Me
$R^5$=Me
$R^6$=H
$R^7$=H
$R^3$=H
$R^4$=Me
Salt: 2HCl
m.p. >300° C.

EXAMPLE 25

X=O
$R^1$=Me
$R^2$=Me
$R^5$=Me
$R^6$=H
$R^7$=H
$R^3$=COPy
$R^4$=Me
m.p. 315° C. (dec.)

EXAMPLE 26

X=O
$R^1$=Me
$R^2$=Me
$R^5$=Me
$R^6$=H
$R^7$=H
$R^3$=$R^e$
$R^4$=Me
m.p. 238–240° C.

EXAMPLE 27

X=O
$R^1$=Me
$R^2$=Me
$R^5$=Me
$R^6$=H
$R^7$=H
$R^3$=$R^a$
$R^4$=Me
Salt: 0.5H$_2$O
m.p. 271° C.

EXAMPLE 28

X=O
$R^1$=$R^e$
$R^2$=H
$R^5$=Me
$R^6$=H
$R^7$=H
$R^3$=$R^e$
$R^4$=Me
m.p. >250° C. (dec.)

EXAMPLE 29

X=O
$R^1$=COiPr
$R^2$=H
$R^5$=Me
$R^6$=H
$R^7$=H
$R^3$=$R^a$
$R^4$=Me
Salt: 0.5H$_2$O
m.p. 251° C.

EXAMPLE 30

X=O
$R^1$=H
$R^2$=H
$R^5$=H
$R^6$=H
$R^7$=H
$R^3$=H
$R^4$=CH$_2$OH
Salt: 2HCl+0.5H$_2$O
m.p. 238–240° C. (dec.)

EXAMPLE 31

X=O
$R^1$=H
$R^2$=H
$R^5$=H
$R^6$=H
$R^7$=H
$R^3$=COPh
$R^4$=CH$_2$OH
m.p. 246° C. (dec.)

EXAMPLE 32

X=O
$R^1$=H
$R^2$=H
$R^5$=H
$R^6$=H
$R^7$=Me
$R^3$=H
$R^4$=CH$_2$OH

EXAMPLE 33

X=O
$R^1$=H $R^2=H$
$R^5=H$
$R^6=H$
$R^7=Me$
$R^3=CHO$
$R^4=CH_2OH$

EXAMPLE 34

$X=O$
$R^1=H$
$R^2=H$
$R^5=H$
$R^6=H$
$R^7=Me$
$R^3=COMe$
$R^4=CH_2OH$

EXAMPLE 35

$X=O$
$R^1=H$
$R^2=H$
$R^5=H$
$R^6=H$
$R^7=H$
$R^3=H$
$R^4=CH_2OMe$
Salt6: 2HCl
m.p. 170° C. (dec.)

EXAMPLE 36

$X=O$
$R^1=H$
$R^2=H$
$R^5=H$
$R^6=H$
$R^7=H$
$R^3=H$
$R^4=CH_2OEt$
Salt: 2HCl
m.p. 165° C. (dec.)

EXAMPLE 37

$X=O$
$R^1=H$
$R^2=H$
$R^5=H$
$R^6=H$
$R^7=H$
$R^3=H$
$R^4=CH_2OiPr$
Salt: 2HCl
m.p. 219–221° C. (dec.)

EXAMPLE 38

$X=O$
$R^1=H$
$R^2=H$
$R^5=H$
$R^6=H$
$R^7=H$
$R^3=H$
$R^4=CH_2OiBu$
Salt: 2HCl+0.5H_2O
m.p. 232–234° C. (dec.)

EXAMPLE 39

$X=O$
$R^1=H$
$R^2=H$
$R^5=H$
$R^6=H$
$R^7=H$
$R^3=H$
$R^4=CH_2O\text{-n-butyl}$

EXAMPLE 40

$X=O$
$R^1=H$
$R^2=H$
$R^5=H$
$R^6=H$
$R^7=H$
$R^3=H$
$R^4=CH_2OtBu$

EXAMPLE 41

$X=O$
$R^1=H$
$R^2=H$
$R^5=H$
$R^6=H$
$R^7=H$
$R^3=H$
$R^4=CH_2O\text{-n-pentyl}$

EXAMPLE 42

$X=O$
$R^1=H$
$R^2=H$
$R^5=H$
$R^6=H$
$R^7=H$
$R^3=H$
$R^4=CH_2O\text{-n-octyl}$

EXAMPLE 43

$X=O$
$R^1=H$
$R^2=H$
$R^5=H$
$R^6=H$
$R^7=H$ $R^3$=H
$R^4$=CH$_2$O-n-decyl
Salt: 2HCl
m.p. 180° C.

EXAMPLE 44

X=O $R^1$=H
$R^2$=H
$R^5$=H
$R^6$=H
$R^7$=H
$R^3$=H
$R^4$=CH$_2$OCH$_2$CH$_2$OMe
Salt: 2HCl
m.p. 221–222° C.

EXAMPLE 45

X=O
$R^1$=H
$R^2$=H
$R^5$=H
$R^6$=H
$R^7$=H
$R^3$=H
$R^4$=CH$_2$OPh
Salt: 2HCl+0.25H$_2$O
m.p. 254–256° C. (dec.)

EXAMPLE 46

X=O
$R^1$=H
$R^2$=H
$R^5$=Me
$R^6$=Me
$R^7$=H
$R^3$=H
$R^4$=CH$_2$OH

EXAMPLE 47

X=O
$R^1$=H
$R^2$=H
$R^5$=Me
$R^6$=Me
$R^7$=H
$R^3$=H
$R^4$=CH$_2$OMe

EXAMPLE 48

X=O
$R^1$=H
$R^2$=H
$R^5$=Me
$R^6$=Me
$R^7$=H
$R^3$=H
$R^4$=CH$_2$OEt

EXAMPLE 49

X=O
$R^1$=H
$R^2$=H
$R^5$=Me
$R^6$=Me
$R^7$=H
$R^3$=H
$R^4$=CH$_2$O-n-propyl

EXAMPLE 50

X=O
$R^1$=H
$R^2$=H
$R^5$=Me
$R^6$=Me
$R^7$=H
$R^3$=H
$R^4$=CH$_2$OiPr

EXAMPLE 51

X=O
$R^1$=H
$R^2$=H
$R^5$=Me
$R^6$=Me
$R^7$=H
$R^3$=H
$R^4$=CH$_2$O-n-pentyl

EXAMPLE 52

X=O
$R^1$=H
$R^2$=H
$R^5$=Me
$R^6$=Me
$R^7$=H
$R^3$=H
$R^4$=CH$_2$O-n-octyl

EXAMPLE 53

X=O
$R^1$=H
$R^2$=H
$R^5$=Me
$R^6$=Me
$R^7$=H
$R^3$=H
$R^4$=CH$_2$O—CH$_2$CH$_2$CH(CH$_3$)$_2$

EXAMPLE 54

X=O
$R^1$=H
$R^2$=H $R^5$=Me
$R^6$=Me
$R^7$=H
$R^3$=H
$R^4$=CH$_2$O—(CH$_2$)$_3$Ph

EXAMPLE 55

X=O
$R^1$=H
$R^2$=H
$R^5$=Me
$R^6$=Me
$R^7$=H
$R^3$=H
$R^4$=CH$_2$O—(CH$_2$)$_3$-cyclohexyl

EXAMPLE 56

X=O
$R^1$=H
$R^2$=H
$R^5$=H
$R^6$=H
$R^7$=Me
$R^3$=CHO
$R^4$=CH$_2$OCHO

EXAMPLE 57

X=O
$R^1$=H
$R^2$=H
$R^5$=H
$R^6$=H
$R^7$=H
$R^3$=H
$R^4$=CH$_2$OCOMe
Salt: H$_2$SO$_4$+0.25H$_2$O
m.p. 230–232° C.

EXAMPLE 58

X=O
$R^1$=H
$R^2$=H
$R^5$=H
$R^6$=H
$R^7$=Me
$R^3$=COMe
$R^4$=CH$_2$OCOMe

EXAMPLE 59

X=O
$R^1$=COMe
$R^2$=H
$R^5$=H
$R^6$=H
$R^7$=H
$R^3$=CH$_2$Ph
$R^4$=CH$_2$OCOMe

EXAMPLE 60

X=O
$R^1$=H
$R^2$=H
$R^5$=H
$R^6$=H
$R^7$=H
$R^3$=H
$R^4$=CH$_2$OCOCH$_2$OH Salt: H$_2$SO$_4$
m.p. 220° C. (dec.)

EXAMPLE 61

X=O
$R^1$=H
$R^2$=H
$R^5$=H
$R^6$=H
$R^7$=H
$R^3$=COtBu
$R^4$=CH$_2$OCOtBu

EXAMPLE 62

X=O
$R^1$=COtBu
$R^2$=H
$R^5$=H
$R^6$=H
$R^7$=H
$R^3$=COOCH$_2$Ph
$R^4$=CH$_2$OCOtBu

EXAMPLE 63

X=O
$R^1$=H
$R^2$=H
$R^5$=H
$R^6$=H
$R^7$=H
$R^3$H
$R^4$=CH$_2$OCOOEt
Salt: H$_2$SO$_4$
m.p. 214° C.

EXAMPLE 64

X=O
$R^1$=H
$R^2$=H
$R^5$=H
$R^6$=H
$R^7$=H
$R^3$=H
$R^4$=CH$_2$OCOCH(Me)(NH$_2$) (L)

EXAMPLE 65

X=O
$R^1$=H
$R^2$=H
$R^5$=H
$R^6$=H
$R^7$=H
$R^3$=H
$R^4$=CH$_2$OCOCH(iPr)(NH$_2$) (L)
Salt: 1.5H$_2$SO$_4$+H$_2$O
m.p. 190° C. (dec.)

EXAMPLE 66

X=O
$R^1$=H
$R^2$=H
$R^5$=H
$R^6$=H
$R^7$=H
$R^3$=H
$R^4$=CH$_2$OCOCH(CH$_2$Ph)(NH$_2$) (DL)
Salt: 2HCl+0.5H$_2$O
m.p. 205° C. (dec.)

EXAMPLE 67

X=O
$R^1$=H
$R^2$=H
$R^5$=H
$R^6$=H
$R^7$=H
$R^3$=Et
$R^4$=CH$_2$SMe
Salt: 2HCl+2/3H$_2$O
m.p. 195–196° C. (dec.)

EXAMPLE 68

X=O
$R^1$=H
$R^2$=H
$R^5$=H
$R^6$=H
$R^7$=H
$R^3$=H
$R^4$=CH$_2$S(O)$_2$Me
Salt: 2HCl
m.p. 252–253° C.

EXAMPLE 69

X=O
$R^1$=H
$R^2$=H
$R^5$=H
$R^6$=H
$R^7$=H
$R^3$=H
$R^4$=CH$_2$NH$_2$
Salt: 3HCl
m.p. 264–265° C. (dec.)

EXAMPLE 70

X=O
$R^1$=H
$R^2$=H
$R^5$=H
$R^6$=H
$R^7$=H
$R^3$=H
$R^4$=CH$_2$NHMe
Salt: 3HCl
m.p. 273–274° C. (dec.)

EXAMPLE 71

X=O
$R^1$=H
$R^2$=H
$R^5$=H
$R^6$=H
$R^7$=H
$R^3$=H
$R^4$=CH$_2$NMe$_2$
Salt: 3HCl+0.5H$_2$O
m.p. 224–225° C.

EXAMPLE 72

X=NH
$R^1$=H
$R^2$=H
$R^5$=H
$R^6$=H
$R^7$=H
$R^3$=H
$R^4$=CH$_2$OH

EXAMPLE 73

X=NH
$R^1$=H
$R^2$=H
$R^5$=H
$R^6$=H
$R^7$=H
$R^3$=H
$R^4$=CH$_2$OEt
Salt: 3HCl
m.p. 130° C. (dec.)

EXAMPLE 74

A compound of the formula

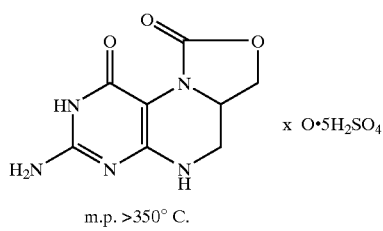

x O·5H$_2$SO$_4$ m.p. >350° C.

EXAMPLE 75

X=O
R$^1$=H
R$^2$=H
R$^5$=H
R$^6$=H
R$^7$=H
R$^3$=H
R$^4$=CH$_2$SEt

EXAMPLE 76

X=O
R$^1$=H
R$^2$=H
R$^5$=H
R$^6$=H
R$^7$=H
R$^3$=H
R$^4$=CH$_2$S-n-propyl

EXAMPLE 77

X=O
R$^1$=H
R$^2$=H
R$^5$=H
R$^6$=H
R$^7$=H
R$^3$=H
R$^4$=CH$_2$S-n-butyl

EXAMPLE 78

X=O
R$^1$=H
R$^2$=H
R$^5$=H
R$^6$=H
R$^7$=Me
R$^3$=H
R$^4$=H

EXAMPLE 79

X=O
R$^1$=H
R$^2$=H
R$^5$=H
R$^6$=H
R$^7$=Me
R$^3$=CHO
R$^4$=H

EXAMPLE 80

X=O
R$^1$=H
R$^2$=H
R$^5$=H
R$^6$=H
R$^7$=H
R$^3$=CSNHPh
R$^4$=H
m.p. >300° C.

EXAMPLE 81

X=O
R$^1$=H
R$^2$=H
R$^5$=H
R$^6$=H
R$^7$=H
R$^3$=CSNHCOPh
R$^4$=H
m.p. >220° C. (dec.)

EXAMPLE 82

X=O
R$^1$=H
R$^2$=H
R$^5$=H
R$^6$=H
R$^7$=H
R$^3$=COPh
R$^4$=H
m.p. >300° C.

EXAMPLE 83

X=O
R$^1$=H
R$^2$=H
R$^5$=H
R$^6$=H
R$^7$=H
R$^3$=COPy
R$^4$=CH$_2$CH$_2$CH$_3$
m.p. 298° C.

EXAMPLE 84

X=O
R$^1$=H
R$^2$=H
R$^5$=H
R$^6$=H $R^7$=H
$R^3$=$R^f$
$R^4$=H
m.p. >300° C.

EXAMPLE 85

X=O
$R^1$=COtBu
$R^2$=H
$R^5$=Ph
$R^6$=H
$R^7$=H
$R^3$=$R^b$
$R^4$=Ph
m.p. 240° C. (dec.)

EXAMPLE 86

X=O
$R^1$=COiPr
$R^2$=H
$R^5$=H
$R^6$=H
$R^7$=H
$R^3$=CO-(2-chlorophenyl)
$R^4$=H

EXAMPLE 87

X=O
$R^1$=COiPr
$R^2$=H
$R^5$=H
$R^6$=H
$R^7$=H
$R^3$=CO-(3-chlorophenyl)
$R^4$=H

EXAMPLE 88

X=O
$R^1$=COiPr
$R^2$=H
$R^5$=H
$R^6$=H
$R^7$=H
$R^3$=CO-(4-chlorophenyl)
$R^4$=H

EXAMPLE 89

X=O
$R^1$=COiPr
$R^2$=H
$R^5$=H
$R^6$=H
$R^7$=H
$R^3$=CO-(2-fluorophenyl)
$R^4$=H

EXAMPLE 90

X=O
$R^1$=COiPr
$R^2$=H
$R^5$=H
$R^6$=H
$R^7$=H
$R^3$=CO-(3-fluorophenyl)
$R^4$=H

EXAMPLE 91

X=O
$R^1$=COiPr
$R^2$=H
$R^5$=H
$R^6$=H
$R^7$=H
$R^3$=CO-(4-fluorophenyl)
$R^4$=H

EXAMPLE 92

X=O
$R^1$=COiPr
$R^2$=H
$R^5$=H
$R^6$=H
$R^7$=H
$R^3$=CO-(4-iodophenyl)
$R^4$=H

EXAMPLE 93

X=O
$R^1$=COiPr
$R^2$=H
$R^5$=H
$R^6$=H
$R^7$=H
$R^3$=CO-(2,3,4-trimethoxyphenyl)
$R^4$=H

EXAMPLE 94

X=O
$R^1$=COiPr
$R^2$=H
$R^5$=H
$R^6$=H
$R^7$=H
$R^3$=CO-(2-methoxyphenyl)
$R^4$=H

EXAMPLE 95

X=O
$R^1$=COiPr
$R^2$=H
$R^5$=H
$R^6$=H
$R^7$=H
$R^3$=COOPh
$R^4$=H

EXAMPLE 96

X=O
$R^1$=COiPr
$R^2$=H
$R^5$=H
$R^6$=H
$R^7$=H
$R^3$=CONMe$_2$
$R^4$=H

EXAMPLE 97

X=O
$R^1$=COiPr
$R^2$=H
$R^5$=H
$R^6$=H
$R^7$=H
$R^3$=CO-(2-thienyl)
$R^4$=H

EXAMPLE 98

X=O
$R^1$=H
$R^2$=H
$R^5$=H
$R^6$=H
$R^7$=H
$R^3$=CO-(2-chlorophenyl)
$R^4$=H

EXAMPLE 99

X=O
$R^1$=H
$R^2$=H
$R^5$=H
$R^6$=H
$R^7$=H
$R^3$=CO-(3-chlorophenyl)
$R^4$=H

EXAMPLE 100

X=O
$R^1$=H
$R^2$=H
$R^5$=H
$R^6$=H
$R^7$=H
$R^3$=CO-(4-chlorophenyl)
$R^4$=H

EXAMPLE 101

X=O
$R^1$=H
$R^2$=H
$R^5$=H
$R^6$=H
$R^7$=H
$R^3$=CO-(2-fluorophenyl)
$R^4$=H

EXAMPLE 102

X=O
$R^1$=H
$R^2$=H
$R^5$=H
$R^6$=H
$R^7$=H
$R^3$=CO-(3-fluorophenyl)
$R^4$=H

EXAMPLE 103

X=O
$R^1$=H
$R^2$=H
$R^5$=H
$R^6$=H
$R^7$=H
$R^3$=CO-(4-fluorophenyl)
$R^4$=H

EXAMPLE 104

X=O
$R^1$=H
$R^2$=H
$R^5$=H
$R^6$=H
$R^7$=H
$R^3$=CO-(4-iodophenyl)
$R^4$=H

EXAMPLE 105

X=O
$R^1$=H
$R^2$=H
$R^5$=H
$R^6$=H
$R^7$=H
$R^3$=CO-(2,3,4-trimethoxyphenyl)
$R^4$=H

EXAMPLE 106

X=O
$R^1$=H
$R^2$=H
$R^5$=H
$R^6$=H
$R^7$=H
$R^3$=CO-(2-methoxyphenyl)
$R^4$=H

EXAMPLE 107

X=O
$R^1$=H $R^2$=H
$R^5$=H
$R^6$=H
$R^7$=H
$R^3$=COOPh
$R^4$=H

EXAMPLE 108

X=O
$R^1$=H
$R^2$=H
$R^5$=H
$R^6$=H
$R^7$=H
$R^3$=CONMe$_2$
$R^4$=H

EXAMPLE 109

X=O
$R^1$=H
$R^2$=H
$R^5$=H
$R^6$=H
$R^7$=H
$R^3$=CO-(2-thienyl)
$R^4$=H

EXAMPLE 110

X=O
$R^1$=H
$R^2$=H
$R^5$=H
$R^6$=H
$R^7$=H
$R^3$=CO-(4-tert-butylphenyl)
$R^4$=H

EXAMPLE 111

X=O
$R^1$=H
$R^2$=H
$R^5$=H
$R^6$=H
$R^7$=H
$R^3$=H
$R^4$=H
Salt: 2HCl

EXAMPLE 112

X=O
$R^1$=COiPr
$R^2$=H
$R^5$=H
$R^6$=H
$R^7$=H
$R^3$=COMe
$R^4$=4-acetylaminophenyl

EXAMPLE 113

X=O
$R^1$=COiPr
$R^2$=H
$R^5$=H
$R^6$=H
$R^7$=H
$R^3$=COMe
$R^4$=Ph

Measurement of inhibition of the activity of purified nitric oxide synthase (NOS)

The coproduct L-citrulline obtained during the formation of NO by purified NOS is determined quantitatively in this activity assay. The substrate of the enzyme reaction employed is $^3$H-radiolabelled L-arginine, which is reacted to give $^3$H-L-citrulline and NO. After the enzyme incubation is complete, resulting L-citrulline is removed from unused L-arginine by means of ion-exchange chromatography of the reaction mixture; the $^3$H activity measured by liquid scintillation then corresponds to the amount of L-citrulline, which is a direct measure of the activity of NOS.

The base medium for carrying out the enzyme reaction is TE buffer (triethanolamine, EDTA, pH 7.0). The final volume of each incubation is 100 μl. The reaction mixture is obtained by mixing the following 6 components on ice:

1. "REA mix" (pH 7.0), which contains triethanolamine, calcium chloride, magnesium chloride, EDTA, L-arginine, calmodulin and flavine adenine dinucleotide (FAD);
2. freshly prepared stock solution of β-nicotinamide adenine dinucleotide phosphate, reduced form (NADPH);
3. (6R)-5,6,7,8-tetrahydro-L-biopterin dihydrochloride stock solution (BH$_4$) or—for experiments without BH$_4$—TE buffer instead of this;
4. purified NO synthase from pig cerebellum or from pig liver;
5. L-[2,3,4,5-$^3$H]-arginine hydrochloride stock solution (1.5–2.6 TBq/mmol);
6. substance to be tested.

The final concentrations of the components in the incubation volume of 100 μl are: Triethanolamine 50 mM, EDTA 0.5 mM, CaCl$_2$ 226 μM, MgCl$_2$ 477 μM, L-arginine 50 μM, calmodulin 0.5 μM, FAD 5 μM, NADPH 1 mM, BH$_4$ (if added) 2 μM, substance to be tested 100 μM. After mixing the components on ice the reaction mixture is immediately incubated in a water bath at 37° C. for 15 minutes. After this incubation time, the reaction is stopped by the addition of 900 μl of ice-cold "stop buffer" (20 mM sodium acetate, 2 mM EDTA, pH 5.5) and the mixture (total volume 1.0 ml) is placed on ice. To separate off the unreacted $^3$H-L-arginine, the mixture is added to an ion-exchange column with 0.8 ml of Dowex AG 50 WX-8 (100–200 mesh), which was previously rinsed and equilibrated with 2 ml of stop buffer. After the application of the sample, the column is eluted twice with 1 ml of water each time. The runnings of the sample and the eluate are collected in scintillation containers and purified (total volume 3 ml). 9 ml of scintillator solution are added to the 3 ml aqueous measuring solution and the homogeneous mixture is measured for 1 minute per sample in a Tricarb 2500 TR (Packard) liquid scintillation counter.

The activity found with the substance to be tested is given in percent of the activity of the control. Each substance is tested for antagonistic action at a concentration of 100 μM in the presence of 2 μM tetrahydrobiopterin and for agonistic action on the NOS in the absence of tetrahydrobiopterin. All incubations are set up in triplicate. Each experiment is repeated three times with various enzyme preparations. Some results are given in the following table.

| Compounds of example | Enzyme from | Citrullin formation (% of the control) |
|---|---|---|
| 57 | pig cerebellum | 66.3 |
| 69 | pig cerebellum | 52.3 |
| 70 | pig cerebellum | 42.5 |
| 71 | pig cerebellum | 46.2 |
| 73 | pig cerebellum | 0.0 |
| 74 | pig cerebellum | 42.6 |
| 80 | pig cerebellum | 1.5 |
| 82 | pig cerebellum | 6.7 |
| 85 | pig cerebellum | 0.0 |

The following examples relate to pharmaceutical preparation forms

EXAMPLE A

Gelatin soft capsules, comprising 100 mg of active compound per capsule:

| | per capsule |
|---|---|
| Active compound | 100 mg |
| Triglyceride mixture fractionated from coconut fat | 400 mg |
| Capsule contents | 500 mg |

EXAMPLE B

Injection solution, comprising 2.0 mg of active compound per ml:

| | per ml |
|---|---|
| Active compound | 2.0 mg |
| Polyethylene glycol 400 | 5.0 mg |
| Sodium chloride | 2.7 mg |
| Water for injection purposes | to 1 ml |

EXAMPLE C

Emulsion, comprising 60 mg of active compound per 5 ml:

| | per 100 ml of emulsion |
|---|---|
| Active compound | 1.2 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavoring | q.s. |
| Water (demineralized or distilled) | to 100 ml |

EXAMPLE D

Rectal pharmaceutical form, comprising 40 mg of active compound per suppository:

| | per suppository |
|---|---|
| Active compound | 40 mg |
| Suppository base mass | to 2 g |

EXAMPLE E

Tablets, comprising 40 mg of active compound per tablet:

| | per tablet |
|---|---|
| Active compound | 40 mg |
| Lactose | 600 mg |
| Corn starch | 300 mg |
| Soluble starch | 20 mg |
| Magnesium stearate | 40 mg |
| | 1000 mg |

EXAMPLE F

Coated tablets, comprising 50 mg of active compound per coated tablet:

| | per coated tablet |
|---|---|
| Active compound | 50 mg |
| Corn starch | 100 mg |
| Lactose | 60 mg |
| sec. calcium phosphate | 30 mg |
| Soluble starch | 5 mg |
| Magnesium stearate | 10 mg |
| Colloidal silicic acid | 5 mg |
| | 260 mg |

EXAMPLE G

For the preparation of the contents of hard gelatin capsules, the following recipes are suitable:

| | | |
|---|---|---|
| a) | Active compound | 100 mg |
| | Corn starch | 300 mg |
| | | 400 mg |
| b) | Active compound | 140 mg |

| | |
|---|---|
| Milk sugar | 180 mg |
| Corn starch | 180 mg |
| | 500 mg |

EXAMPLE H

Drops can be prepared according to the following recipe (100 mg of active compound in 1 ml=20 drops):

| | |
|---|---|
| Active compound | 10 g |
| Methyl benzoate | 0.07 g |
| Ethyl benzoate | 0.03 g |
| Ethanol, 96% strength | 5 ml |
| Demineralized water | to 100 ml |

What is claimed is:

1. A method for the inhibition of nitric oxide production in a mammal, comprising administering to a mammal in need of such inhibition an effective amount of a pteridine compound of the formula I

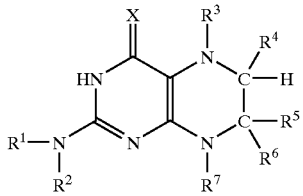
(I)

X is O or NH;

$R^1$ is hydrogen, methyl, $(C_1-C_5)$-alkanoyl, nicotinoyl or (1-methyl-3-pyridinio)carbonyl;

$R^2$ is hydrogen or methyl;

$R^3$ is hydrogen, methyl, ethyl, benzyl, $(C_1-C_5)$-alkanoyl, unsubstituted benzoyl, substituted benzoyl, pyridoyl, thienylcarbonyl, one of the radicals

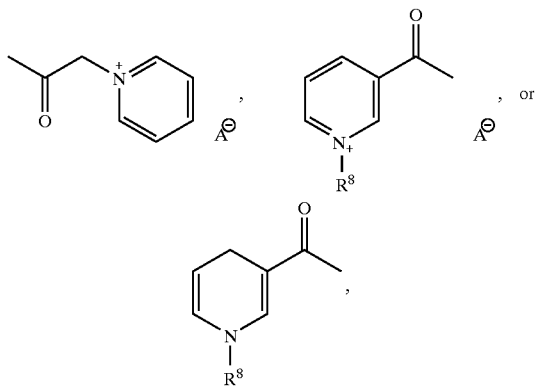

the radical $R^9R^{9a}N$—CO—, the radical $R^9R^{9a}N$—CS—, phenoxycarbonyl or benzyloxycarbonyl, wherein when benzoyl is substituted with a halogen, the halogen is fluorine, chlorine, or bromine;

$R^4$ is hydrogen, $(C_2-C_5)$-alkyl, unsubstituted phenyl, substituted phenyl or the radical $R^{4a}$—$CH_2$—, wherein when phenyl is substituted with a halogen, the halogen is fluorine, chlorine, or bromine;

$R^{4a}$ is hydrogen, $(C_1-C_4)$-alkylmercapto, the radical —$S(O)_mR^{10}$, where m is the number 1 or 2, the radical —$NR^{11}R^{12}$ or the radical —$OR^{13}$, or $R^3$ and $R^{4a}$ together are the group —CO—O—, its carbonyl carbon atom being bonded to the 5-position of the pteridine molecule;

$R^5$ is hydrogen or phenyl;

$R^6$ is hydrogen;

$R^7$ is hydrogen or methyl;

$R^8$ is $(C_1-C_{10})$-alkyl or benzyl;

$R^9$ is hydrogen, $(C_1-C_6)$-alkyl, cyclohexyl, phenyl or benzoyl;

$R^{9a}$ is hydrogen, methyl or ethyl;

$R^{10}$ is methyl;

$R^{11}$ and $R^{12}$ independently of one another are hydrogen or methyl;

$R^{13}$ is hydrogen, $(C_1-C_{10})$-alkyl, 2-methoxyethyl, phenyl, 3-phenylpropyl, 3-cyclohexylpropyl, $(C_1-C_5)$-alkanoyl, hydroxyacetyl, 2-amino-$(C_2-C_6)$-alkanoyl which is unsubstituted or substituted in the alkyl moiety by a phenyl radical, or $((C_1-C_2)$-alkoxy)carbonyl;

$A^\ominus$ is a pharmacologically tolerable anion;

or a tautomeric form or pharmacologically tolerable salt thereof with the proviso that said pteridine compound is not 6-methyltetrahydropterin or 2-amino-5,6,7,8-tetrahydro-4(1)-pterinidone.

2. A method for treating at least one of pathological blood pressure decreases, inflammatory disorders, infarct damage, reperfusion damage, transplant rejection reactions, Alzheimer's disease, epilepsy, migraines, neuritis, encephalomyelitis, viral neurodegenerative diseases, hyperalgesia, kidney failure, nephritides, myocarditis, cardiomyopathy, disease of the stomach, uterus or placenta, deficiencies in sperm mobility, type 1 diabetes or insulin-dependent diabetes mellitus, atherosclerosis, and glutamate-induced neurotoxicity after cerebral ischemia, which comprises administering to a mammal in need of such treatment, an effective amount of pteridine compound of the formula I

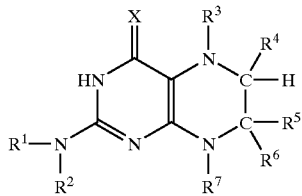

in which

X is O or NH;

$R^1$ is hydrogen, methyl, $(C_1-C_5)$-alkanoyl, nicotinoyl or (1-methyl-3-pyridinio)carbonyl;

$R^2$ is hydrogen or methyl;

$R^3$ is hydrogen, methyl, ethyl, benzyl, $(C_1-C_5)$-alkanoyl, unsubstituted benzoyl, substituted benzoyl, pyridoyl, thienylcarbonyl, one of the radicals

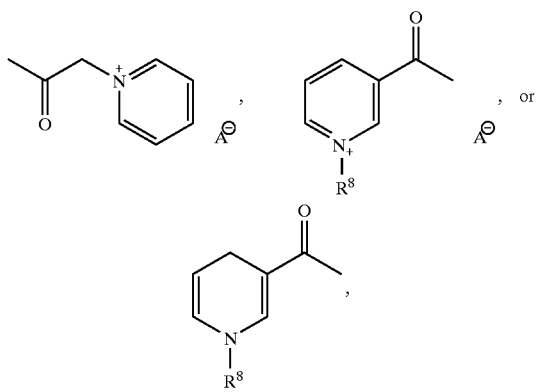

the radical $R^9R^{9a}N\text{—}CO\text{—}$, the radical $R^9R^{9a}N\text{—}CS\text{—}$, phenoxycarbonyl, or benzyloxycarbonyl;

$R^4$ is hydrogen, $(C_2\text{-}C_5)$-alkyl, unsubstituted phenyl, substituted phenyl or the radical $R^{4a}\text{—}CH_2\text{—}$;

$R^{4a}$ is hydrogen, $(C_1\text{-}C_4)$-alkylmercapto, the radical $\text{—}S(O)_mR^{10}$, where m is the number 1 or 2, the radical $\text{—}NR^{11}R^{12}$ or the radical $\text{—}OR^{13}$, or $R^3$ and $R^{4a}$ together are the group $\text{—}CO\text{—}O\text{—}$, its carbonyl carbon atom being bonded to the 5-position of the pteridine molecule;

$R^5$ is hydrogen or phenyl;

$R^6$ is hydrogen;

$R^7$ is hydrogen or methyl;

$R^8$ is $(C_1\text{-}C_{10})$-alkyl or benzyl;

$R^9$ is hydrogen, $(C_1\text{-}C_6)$-alkyl, cyclohexyl, phenyl or benzoyl;

$R^{9a}$ is hydrogen, methyl or ethyl;

$R^{10}$ is methyl;

$R^{11}$ and $R^{12}$ independently of one another are hydrogen or methyl;

$R^{13}$ is hydrogen, $(C_1\text{-}C_{10})$-alkyl, 2-methoxyethyl, phenyl, 3-phenylpropyl, 3-cyclohexylpropyl, $(C_1\text{-}C_5)$-alkanoyl, hydroxyacetyl, 2-amino-$(C_2\text{-}C_6)$-alkanoyl, which is unsubstituted or substituted in the alkyl moiety by a phenyl radical, or $((C_1\text{-}C_2)$-alkoxy)carbonyl;

$A^\ominus$ is a pharmacologically tolerable anion;

or a tautomeric form or pharmacologically tolerable salt thereof with the proviso that said pteridine compound is not 6-methyltetrahydropterin or 2-amino-5,6,7,8-tetrahydro-4(1)-pterinidone.

3. A method as claimed in claim 2, wherein X is oxygen.

4. A method as claimed in claim 2, wherein $R^3$ is hydrogen, $(C_1\text{-}C_5)$-alkanoyl, unsubstituted benzoyl, mono-, di- or trisubstituted benzoyl, thienylcarbonyl, nicotinoyl, one of the radicals

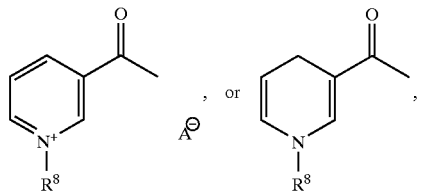

or $R^9NH\text{—}CO\text{—}$, $R^9NH\text{—}CS\text{—}$ or $(CH_3)_2N\text{—}CO\text{—}$.

5. A method as claimed in claim 2, wherein $R^4$ is hydrogen, phenyl, phenyl substituted by acetylamino group or the radical $R^{4a}\text{—}CH_2\text{—}$.

6. The method according to claim 5, wherein $R^{4a}$ is hydrogen or the radical $\text{—}OR^{13}$.

7. The method according to claim 5, wherein $R^{13}$ is $(C_1\text{-}C_{10})$-alkyl or $(C_1\text{-}C_5)$-alkanoyl.

8. A method as claimed in claim 2 for the treatment of disorders of the nervous system selected from the group consisting of Alzheimer's disease, epilepsy and migraine.

9. The method according to claim 2, wherein in formula I,

X is O, $R^1$, $R^2$, $R^3$, $R^5$, $R^6$, and $R^7$ are hydrogen, and $R^4$ is $CH_2OCOMe$.

10. The method according to claim 2, wherein in formula I,

X is O, $R^1$, $R^2$, $R^3$, $R^5$, $R^6$, and $R^7$ are hydrogen, and $R^4$ is $CH_2NH_2$.

11. The method according to claim 2, wherein in formula I,

X is O, $R^1$, $R^2$, $R^3$, $R^5$, $R^6$, and $R^7$ are hydrogen, and $R^4$ is $CH_2NHMe$.

12. The method according to claim 2, wherein in formula I,

X is O, $R^1$, $R^2$, $R^3$, $R^5$, $R^6$, and $R^7$ are hydrogen, and $R^4$ is $CH_2NMe_2$.

13. The method according to claim 2, wherein in formula I,

X is NH, $R^1$, $R^2$, $R^3$, $R^5$, $R^6$, and $R^7$ are hydrogen, and $R^4$ is $CH_2OEt$.

14. The method according to claim 2, wherein in the structure of formula I is

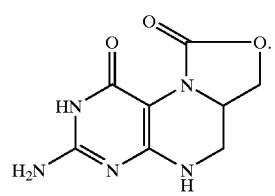

15. The method according to claim 2, wherein in formula I,

X is O, $R^1$, $R^2$, $R^4$, $R^5$, $R^6$, and $R^7$ are hydrogen, and $R^3$ is CSNHPh.

16. The method according to claim 2, wherein in formula I,

X is O, $R^1$, $R^2$, $R^4$, $R^5$, $R^6$, and $R^7$ are hydrogen, and $R^3$ is COPh.

17. The method according to claim 2, wherein in formula I,

X is O, $R^1$ is COtBu, $R^2$, $R^6$ and $R^7$ are hydrogen, $R^3$ is

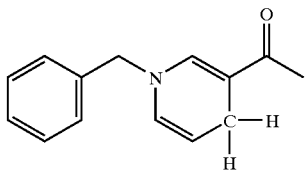

and $R^4$ and $R^5$ are phenyl.

18. The method according to claim 2, wherein the inflammatory disorder is rheumatoid arthritis.

19. A method for treating at least one of pathological blood pressure decreases, inflammatory disorders, infarct damage, reperfusion damage, and transplant rejection reactions, which comprises administering to a mammal in need of such treatment, an effective amount of a pteridine compound of the formula I

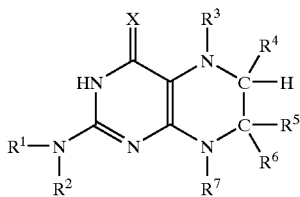

in which

X is O or NH;

$R^1$ is hydrogen, methyl, $(C_1-C_5)$-alkanoyl, nicotinoyl or (1-methyl-3-pyridinio)carbonyl;

$R^2$ is hydrogen or methyl;

$R^3$ is hydrogen, methyl, ethyl, benzyl, $(C_1-C_5)$-alkanoyl, unsubstituted benzoyl, substituted benzoyl, pyridoyl, thienylcarbonyl, one of the radicals

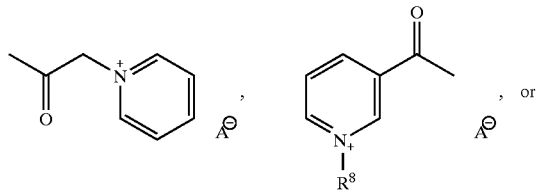, or

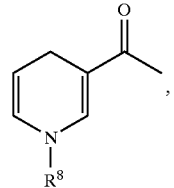, the radical $R^9R^{9a}N$—CO—, the radical $R^9R^{9a}N$—CS—, phenoxycarbonyl, or benzyloxycarbonyl;

$R^4$ is hydrogen, $(C_2-C_5)$-alkyl, unsubstituted phenyl, substituted phenyl or the radical $R^{4a}$—$CH_2$—;

$R^{4a}$ is hydrogen, $(C_1-C_4)$-alkylmercapto, the radical —$S(O)_m R^{10}$, where m is the number 1 or 2, the radical —$NR^{11}R^{12}$ or the radical —$OR^{13}$, or $R^3$ and $R^{4a}$ together are the group —CO—O—, its carbonyl carbon atom being bonded to the 5-position of the pteridine molecule;

$R^5$ is hydrogen or phenyl;

$R^6$ is hydrogen;

$R^7$ is hydrogen or methyl;

$R^8$ is $(C_1-C_{10})$-alkyl or benzyl;

$R^9$ is hydrogen, $(C_1-C_6)$-alkyl, cyclohexyl, phenyl or benzoyl;

$R^{9a}$ is hydrogen, methyl or ethyl;

$R^{10}$ is methyl;

$R^{11}$ and $R^{12}$ independently of one another are hydrogen or methyl;

$R^{13}$ is hydrogen, $(C_1-C_{10})$-alkyl, 2-methoxyethyl, phenyl, 3-phenylpropyl, 3-cyclohexylpropyl, $(C_1-C_5)$-alkanoyl, hydroxyacetyl, 2-amino-$(C_2-C_6)$-alkanoyl, which is unsubstituted or substituted in the alkyl moiety by a phenyl radical, or $((C_1-C_2)$-alkoxy)carbonyl;

$A^8$ is a pharmacologically tolerable anion;

or a tautomeric form or pharmacologically tolerable salt thereof with the proviso that said pteridine compound is not 6-methyltetrahydropterin or 2-amino-5,6,7,8-tetrahydro-4 (1)-pterinidone.

20. The method according to claim 19, wherein the pathological blood pressure decrease is due to one of septic shock or hemorrhagic shock.

21. The method according to claim 19, wherein the pathological blood pressure decrease is due to tumor therapy with cytokines.

22. The method according to claim 19, wherein the inflammatory disorder is ulcerative colitis.

23. A method of claim 19, wherein the mammal treated is susceptible to the development or the reoccurrence of pathological blood pressure decreases, inflammatory disorders, infarct damage, reperfusion damage, or transplant rejection reactions.

* * * * *

UNITED STATES PATENT AND TRADEMARK OFFICE
CERTIFICATE OF CORRECTION

PATENT NO. : 6,858,612 B1
APPLICATION NO. : 09/357212
DATED : February 22, 2005
INVENTOR(S) : Wolfgang Pfleiderer et al.

It is certified that error appears in the above-identified patent and that said Letters Patent is hereby corrected as shown below:

On the Title Page:
Item (73), Assignee: Vasopharm Buitech GmbH, should read --Vasopharm Biotech GmbH--.

Signed and Sealed this

Thirty-first Day of October, 2006

JON W. DUDAS
*Director of the United States Patent and Trademark Office*